United States Patent
Chodorowski-Kimmes

(10) Patent No.: US 10,959,935 B2
(45) Date of Patent: Mar. 30, 2021

(54) HAIR DYEING PROCESS COMPRISING A BLOCK POLYMER BEARING PHOSPHONIC ACID GROUPS AND A PIGMENT

(71) Applicant: L'ORÉAL, Paris (FR)

(72) Inventor: Sandrine Chodorowski-Kimmes, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/500,718

(22) PCT Filed: Apr. 9, 2018

(86) PCT No.: PCT/EP2018/059045
§ 371 (c)(1),
(2) Date: Oct. 3, 2019

(87) PCT Pub. No.: WO2018/185344
PCT Pub. Date: Oct. 11, 2018

(65) Prior Publication Data
US 2020/0188283 A1    Jun. 18, 2020

(30) Foreign Application Priority Data
Apr. 7, 2017   (FR) ...................................... 1753072

(51) Int. Cl.
| | | |
|---|---|---|
| *A61Q 5/10* | (2006.01) | |
| *A61K 8/81* | (2006.01) | |
| *A61K 8/25* | (2006.01) | |
| *A61K 8/898* | (2006.01) | |

(52) U.S. Cl.
CPC .............. *A61K 8/8152* (2013.01); *A61K 8/25* (2013.01); *A61K 8/898* (2013.01); *A61K 2800/432* (2013.01)

(58) Field of Classification Search
CPC ........ A61Q 5/10; A61K 8/817; A61K 8/8152; A61K 2800/43; A61K 8/585; A61K 8/24; A61K 8/90; A61K 8/894; A61K 8/89; A61K 31/13; A61K 8/898

USPC .............................. 8/405, 202; 132/405, 202
See application file for complete search history.

(56) References Cited

U.S. PATENT DOCUMENTS

| | | | |
|---|---|---|---|
| 6,106,577 A | | 8/2000 | Audousset et al. |
| 2006/0159644 A1* | | 7/2006 | Panangatte ............ A61K 8/898 |
| | | | 424/70.11 |
| 2017/0252283 A1 | | 9/2017 | Lion et al. |

FOREIGN PATENT DOCUMENTS

| | | |
|---|---|---|
| FR | 2 741 530 A1 | 5/1997 |
| FR | 2 946 872 A1 | 12/2010 |
| WO | WO 2015/197778 A1 | 12/2015 |
| WO | WO 2017/108600 A1 | 6/2017 |

OTHER PUBLICATIONS

STIC Search Report dated May 28, 2020.*
International Search Report dated May 28, 2018 in PCT/EP2018/059045 filed on Apr. 9, 2018.

* cited by examiner

*Primary Examiner* — Elisa B Elhilo
(74) *Attorney, Agent, or Firm* — Oblon, McClelland, Maier & Neustadt, L.L.P.

(57) ABSTRACT

The invention relates to a hair dyeing process comprising at least one pigment, at least one additional component selected from cross linking agents and/or plasticizers and at least one block polymer comprising: a first block with a glass transition temperature (Tg) of greater than or equal to 40° C. derived from a monomer $CH_2=C(R_1)-COOR2$ in which $R_1=H$ or methyl, $R_2=C_4$ to $C_{12}$ cycloalkyl group; and a second block with a glass transition temperature (Tg) of less than or equal to 20° C. derived from a vinylphosphonic acid and from a monomer $CH2=C(R_1)-COOR_3$ in which $R_1=H$ or methyl, $R_3=$linear or branched $C_1$ to $C_6$ unsubstituted alkyl group, with the exception of a tert-butyl group or a methoxyethyl group.

31 Claims, No Drawings

HAIR DYEING PROCESS COMPRISING A BLOCK POLYMER BEARING PHOSPHONIC ACID GROUPS AND A PIGMENT

The present invention relates to a hair dyeing process comprising a pigment and a block polymer bearing a phosphonic acid group.

Block polymers, especially based on isobornyl (meth) acrylate, isobutyl acrylate and acrylic acid, which are advantageous in the field of cosmetics for their film-forming properties and their good persistence and gloss, are known from patent application EP-A-1 882 709. However, it is desirable to improve the cosmetic properties of such block polymers, in particular the transfer-resistance and tack-free properties, especially when the film-forming deposit comes into contact with the fingers. It is also desirable to improve the persistence properties of the film on contact with oils or sebum.

In the field of dyeing keratin fibres, it is already known practice to dye keratin fibres via various techniques using direct dyes for non-permanent dyeing, or dye precursors for permanent dyeing.

Non-permanent dyeing or direct dyeing consists in dyeing keratin fibres with dye compositions containing direct dyes. These dyes are coloured and colouring molecules that have affinity for keratin fibres. They are applied to the keratin fibres for a time necessary to obtain the desired colouring, and are then rinsed out.

The standard dyes that are used are, in particular, dyes of the nitrobenzene, anthraquinone, nitropyridine, azo, xanthene, acridine, azine or triarylmethane type, or natural dyes.

Some of these dyes may be used under lightening conditions, which enables the production of colourings that are visible on dark hair.

It is also known practice to dye keratin fibres permanently via oxidation dyeing. This dyeing technique consists in applying to the keratin fibres a composition containing dye precursors such as oxidation bases and couplers. Under the action of an oxidizing agent, these precursors, form one or more coloured substances in the hair.

The variety of molecules used as oxidation bases and couplers allows a wide range of colours to be obtained, and the colourings resulting therefrom are generally permanent, strong and resistant to external agents, especially to light, bad weather, washing, perspiration and rubbing.

In order to be visible on dark hair, these two dyeing techniques require prior or simultaneous bleaching of the keratin fibres. This bleaching step, performed with an oxidizing agent such as hydrogen peroxide or persalts, results in appreciable degradation of the keratin fibres, which impairs their cosmetic properties. The hair then has a tendency to become coarse, more difficult to disentangle and more brittle.

Another dyeing method consists in using pigments. Specifically, the use of pigment at the surface of the keratin fibres generally makes it possible to obtain visible colourings on dark hair, since the surface pigment masks the natural colour of the fibre. The use of pigment for dyeing keratin fibres is described, for example, in patent application FR 2 741 530, which recommends using for the temporary dyeing of keratin fibres a composition comprising at least one dispersion of film-forming polymer particles comprising at least one acid function and at least one pigment dispersed in the continuous phase of said dispersion.

The colourings obtained via this dyeing method have the drawback of being removed from the very first shampoo wash.

It is moreover known from patent application FR 2 907 678 to perform coloured coating of the hair using a composition comprising a polysiloxane/polyurea block copolymer and a pigment. However, with such a composition, the coating results obtained are not always very homogeneous and the individualization of the hair strands is not always very good.

It is also known practice from patent EP 1 392 222 to use a cosmetic composition for caring for and/or treating keratin materials, comprising a supramolecular polymer comprising a polymer backbone and at least two groups that are capable of forming at least three hydrogen bonds, and from patent EP 1 435 900 to use a hair composition comprising a supramolecular polymer comprising a polymer backbone and at least two groups that are capable of forming at least three hydrogen bonds and a surfactant or a hair-conditioning agent.

Thus, the aim of the present invention is to provide a composition for dyeing keratin fibres such as the hair, which makes it possible to obtain coloured coatings that show good resistance to attacking factors such as brushing, do not leach, are resistant to sweat, light and bad weather, and are fast with respect to shampoo washing and to the various attacking factors which hair may be subjected, without degrading the keratin fibres, and while at the same time keeping the hair strands perfectly individualized.

One subject of the present invention is a hair dyeing process which comprises the application to the hair of (i) at least one pigment and (ii) of at least one block polymer comprising:

at least one first block with a glass transition temperature (Tg) of greater than or equal to 40° C. and obtained from at least one (meth)acrylate monomer of formula $CH_2=C(R_1)-COOR_2$ in which $R_1$ represents H or a methyl radical and $R_2$ represents a $C_4$ to $C_{12}$ cycloalkyl group; and at least one second block with a glass transition temperature (Tg) of less than or equal to 20° C. and is obtained from at least one vinylphosphonic acid monomer of formula (I) defined below and from at least one (meth)acrylate monomer of formula $CH_2=C(R_1)-COOR_3$ in which $R_1$ represents H or a methyl radical and $R_3$ represents either a linear or branched $C_1$ to $C_6$ unsubstituted alkyl group, with the exception of a tert-butyl group or a methoxyethyl group, and (iii) at least one additional compounds selected from plasticizers and/or crosslinking agents Such a block polymer is referred to hereinbelow as a phosphonic polymer.

A subject of the invention is also a composition comprising at least one pigment and at least one phosphonic polymer as described previously, and at least one additional compound selected from plasticizers and/or cross linking agents.

According to one embodiment of the process according to the invention, a composition obtained by the mixing (extemporaneous) of at least one pigment, of a composition comprising a phosphonic polymer as described previously and of an additional component chosen from polyamine compounds bearing several primary amine and/or secondary amine groups, amino alkoxysilanes, or a composition containing same and comprising a physiologically acceptable medium, is applied to the hair, the composition(s) used being anhydrous when the additional component is an amino alkoxysilane, the pigment(s) being present in the mixture or in one and/or the other of the compositions. According to another embodiment, the pigment is present in another composition.

According to one embodiment of the process according to the invention, the mixing of the composition comprising the phosphonic polymer and of the additional component, or of the composition containing same, is performed in a time of between 1 minute and 24 hours before its application to the keratin materials, and preferably between 5 and 30 minutes.

According to a first embodiment of the process according to the invention, a composition derived from the mixing (extemporaneous) of a composition comprising a phosphonic polymer as described previously and of an additional component as defined below, or of a composition containing same, is applied to the hair, the pigment(s) being present in the mixture or in one and/or the other of the compositions. According to another embodiment, the pigment is present in another composition.

According to a second embodiment of the process according to the invention, a composition comprising a phosphonic polymer as described previously and an additional component as defined below, or a composition containing same, are applied sequentially to the hair, the pigment(s) being present in the mixture or in one and/or the other of the compositions. According to another embodiment, the pigment is present in another composition.

A subject of the invention is also a composition, obtained by mixing a composition comprising, in a physiologically acceptable medium, said phosphonic polymer and an additional component as defined previously or a composition containing same, the composition being anhydrous when the additional compound is an amino alkoxysilane, the pigment(s) being present in the mixture or in one and/or the other of the compositions. According to another embodiment, the pigment is present in another composition.

A subject of the invention is also a kit comprising a first composition comprising said phosphonic polymer as described previously and a second composition comprising an additional component as defined previously, the first and second compositions comprising at least one pigment and each being packaged in a separate packaging assembly, the compositions being anhydrous when the additional compound is an amino alkoxysilane.

The composition packaging assembly is, in a known manner, any packaging that is suitable for storing cosmetic compositions (in particular a bottle, tube, spray bottle or aerosol bottle).

The block polymer used in the invention comprises:
at least one first block with a glass transition temperature (Tg) of greater than or equal to 40° C. and obtained from at least one (meth)acrylate monomer of formula $CH_2=C(R_1)—COOR_2$ in which $R_1$ represents H or a methyl radical and $R_2$ represents a $C_4$ to $C_{12}$ cycloalkyl group; and
at least one second block with a glass transition temperature (Tg) of less than or equal to 20° C. and is obtained from at least one vinylphosphonic acid monomer of formula (I) defined below and from at least one (meth)acrylate monomer of formula $CH_2=C(R_1)—COOR_3$ in which $R_1$ represents H or a methyl radical and $R_3$ represents a linear or branched $C_1$ to $C_6$ unsubstituted alkyl group, with the exception of a tert-butyl group.

The glass transition temperatures indicated for the first and second blocks may be theoretical Tg values determined from the theoretical Tg values of the constituent monomers of each of the blocks, which may be found in a reference manual such as the Polymer Handbook, 3rd Edition, 1989, John Wiley, according to the following relationship, known as Fox's law:

$$1/Tg = \sum_i (\omega_i / Tg_i),$$

$\omega_i$ being the mass fraction of the monomer i in the block under consideration and $Tg_i$ being the glass transition temperature of the homopolymer of the monomer i.

Unless otherwise indicated, the Tg values indicated for the first and second blocks in the present patent application are theoretical Tg values.

The difference between the glass transition temperatures of the first and second blocks is generally greater than 20° C., preferably greater than 40° C. and better still greater than 60° C.

In the present invention, the expression:
"between . . . and . . . " means a range of values in which the limits mentioned are excluded, and
"from . . . to . . . " and "ranging from . . . to . . . " mean a range of values in which the limits are included.

First Block

The block polymer used according to the invention has a first block with a glass transition temperature (Tg) of greater than or equal to 40° C., for example a Tg ranging from 40 to 150° C., and obtained from at least one (meth)acrylate monomer of formula $CH_2=C(R_1)—COOR_2$ in which $R_1$ represents H or a methyl radical, and $R_2$ represents a $C_4$ to $C_{12}$ cycloalkyl group.

Preferably, said first block has a Tg of greater than or equal to 60° C., ranging, for example, from 60° C. to 140° C., especially ranging from 80° C. to 120° C.

The monomers present in the first block of the polymer and the proportions thereof are preferably chosen such that the glass transition temperature of the first block is greater than or equal to 40° C., and especially in accordance with that described previously.

According to a preferred embodiment, the first block of the polymer is obtained from at least one acrylate monomer of formula $CH_2=CH—COOR_2$ in which $R_2$ represents a $C_4$ to $C_{12}$ cycloalkyl group, and from at least one methacrylate monomer of formula $CH_2=C(CH_3)—COOR'_2$ in which $R'_2$ represents a $C_4$ to $C_{12}$ cycloalkyl group.

The first block of the polymer may be obtained exclusively with said acrylate monomer and said methacrylate monomer.

The acrylate monomer and the methacrylate monomer are preferably used in acrylate/methacrylate mass proportions of between 30/70 and 70/30, preferably between 40/60 and 60/40, especially between 45/55 and 55/45.

The proportion of the first block in the block polymer advantageously ranges from 60% to 80% and better still from 65% to 75% by weight of the polymer.

According to a preferred embodiment, the first block of the polymer is obtained by polymerization of isobornyl methacrylate and isobornyl acrylate.

The first block of the polymer may also comprise an additional monomer chosen from linear or branched $C_8$-$C_{22}$ alkyl (meth)acrylates (i.e. comprising a $C_8$-$C_{22}$ alkyl group), for instance 2-ethylhexyl acrylate, 2-ethylhexyl methacrylate, lauryl acrylate, lauryl methacrylate, behenyl acrylate, behenyl methacrylate, stearyl acrylate and stearyl methacrylate.

Said additional monomer may be present in a content ranging from 0.1% to 15% by weight and preferably ranging from 0.1% to 5% by weight, relative to the total weight of the monomers of the first block of said block polymer.

According to one embodiment, the first block of said block polymer does not contain any additional monomer.

Second Block

The block polymer used according to the invention has a second block with a glass transition temperature (Tg) of less than or equal to 20° C., for example a Tg ranging from −100 to 20° C., and is obtained from at least one vinylphosphonic acid monomer of formula (I) defined below and from at least one (meth)acrylate monomer of formula $CH_2=C(R_1)$—$COOR_3$ in which $R_1$ represents H or a methyl radical and $R_3$ represents a linear or branched $C_1$ to $C_6$ unsubstituted alkyl group, with the exception of a tert-butyl group, or a methoxyethyl group.

Preferably, said second block has a Tg of less than or equal to 10° C., especially ranging from −80° C. to 15° C. and better still less than or equal to 0° C., for example ranging from −100° C. to 0° C., especially ranging from −30° C. to 0° C.

The monomers present in the second block of the polymer and the proportions thereof are preferably chosen such that the glass transition temperature of the second block is less than or equal to 20° C., and especially in accordance with that described previously.

The vinylphosphonic acid monomer corresponds to the following formula (I):

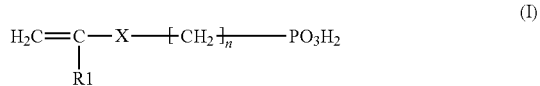

in which:
$R_1$ denotes H or —$CH_3$;
X denotes a covalent bond and n denotes an integer ranging from 0 to 14;
or X denotes a —COO— group and n denotes an integer ranging from 2 to 6.

Advantageously, for the monomer of formula (I), X denotes a covalent bond and n is an integer ranging from 0 to 6 or X denotes a —COO— group and n is an integer ranging from 2 to 4.

Preferentially, for the monomer of formula (I):

$R_1$=H

X denotes a covalent bond and n is an integer ranging from 0 to 4.

As examples of monomers of formula (I), mention may be made of:
vinylphosphonic acid;
3-butenylphosphonic acid;
4-pentenylphosphonic acid;
10-undecenylphosphonic acid;
11-dodecenylphosphonic acid;
2-phosphonoethyl ester of 2-propenoic acid;
2-phosphonoethyl ester of 2-methyl-2-propenoic acid.

Preferably, monomer (I) is vinylphosphonic acid.

The preferred monomers with a Tg of less than or equal to 20° C. are isobutyl acrylate, ethyl acrylate, n-butyl acrylate and methoxyethyl acrylate, or mixtures thereof in all proportions.

The second block of the polymer may be obtained exclusively with the vinylphosphonic acid monomer (I) and said acrylate monomer.

The vinylphosphonic acid monomer (I) and the acrylate monomer are preferably used in acrylate/vinylphosphonic acid monomer (I) mass proportions ranging from 1 to 10, preferentially ranging from 2 to 9, especially ranging from 3 to 8 or alternatively ranging from 4 to 7.

The proportion of the second block in the block polymer advantageously ranges from 20% to 40% and better still from 25% to 35% by weight of the polymer.

According to a preferred embodiment, the second block of the polymer is obtained by polymerization of vinylphosphonic acid and isobutyl acrylate.

The second block of the polymer may also comprise an additional silicone monomer of formula (II) (referred to hereinbelow as a silicone monomer) below:

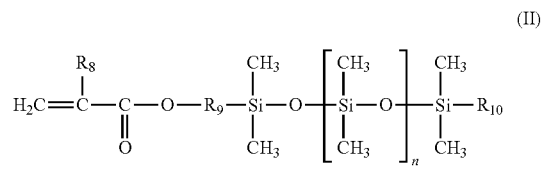

in which:
$R_8$ denotes a hydrogen atom or a methyl group; preferably methyl;
$R_9$ denotes a linear or branched, preferably linear, divalent hydrocarbon-based group containing from 1 to 10 carbon atoms, preferably containing from 2 to 4 carbon atoms, and optionally containing one or two —O— ether bonds; preferably an ethylene, propylene or butylene group;
$R_{10}$ denotes a linear or branched alkyl group containing from 1 to 10 carbon atoms, especially from 2 to 8 carbon atoms; preferably methyl, ethyl, propyl, butyl or pentyl;
n denotes an integer ranging from 1 to 300, preferably ranging from 3 to 200 and preferentially ranging from 5 to 100.

Monomer (II) is a polydimethylsiloxane bearing a mono (meth)acryloyloxy end group.

Use may be made in particular of monomethacryloyloxypropyl polydimethylsiloxanes such as those sold under the names MCR-M07, MCR-M17, MCR-M11 and MCR-M22 by Gelest Inc. or the silicone macromonomers sold under the names X-22-2475, X-22-2426 and X-22-174DX by Shin-Etsu.

Monomer (II) may be present in the second block of the block polymer in a content ranging from 0.1% to 15% by weight, relative to the total weight of the monomers of the second block of said block polymer, and preferably ranging from 0.1% to 5%.

According to one embodiment, the second block of said block polymer does not contain any additional monomer.

Preferably, the polymer used according to the invention comprises at least, or even consists of, isobornyl acrylate and isobornyl methacrylate monomers in the first block and vinylphosphonic acid and isobutyl acrylate monomers in the second block.

Preferably, the polymer comprises at least, or even consists of, isobornyl acrylate and isobornyl methacrylate monomers in a mass proportion ranging from 30/70 to 70/30 in the first block and isobutyl acrylate and vinylphosphonic acid monomers in the second block.

Preferably, the polymer comprises at least, or even consists of, isobornyl acrylate and isobornyl methacrylate monomers in a mass proportion ranging from 40/60 to 60/40 in the first block and isobutyl acrylate and vinylphosphonic acid monomers in the second block.

Preferably, the polymer comprises at least, or even consists of, isobornyl acrylate and isobornyl methacrylate monomers in a mass proportion ranging from 45/55 to 55/45 in the first block and isobutyl acrylate and vinylphosphonic acid monomers in the second block.

Preferably, the polymer comprises at least, or even consists of, isobornyl acrylate and isobornyl methacrylate monomers in a mass proportion ranging from 30/70 to 70/30 in the first block and isobutyl acrylate and vinylphosphonic acid monomers in the second block, the first block representing between 65% and 75% by weight of the polymer, and especially 70% by weight.

Preferably, the polymer comprises at least, or even consists of, isobornyl acrylate and isobornyl methacrylate monomers in a mass proportion ranging from 40/60 to 60/40 in the first block and isobutyl acrylate and vinylphosphonic acid monomers in the second block, the first block representing between 65% and 75% by weight of the polymer, and especially 70% by weight.

Preferably, the polymer comprises at least, or even consists of, isobornyl acrylate and isobornyl methacrylate monomers in a mass proportion ranging from 45/55 to 55/45 in the first block and isobutyl acrylate and vinylphosphonic acid monomers in the second block, the first block representing between 65% and 75% by weight of the polymer, and especially 70% by weight.

Preferably, the polymer comprises at least, or even consists of, isobornyl acrylate and isobornyl methacrylate monomers in a mass proportion ranging from 30/70 to 70/30 in the first block and isobutyl acrylate and vinylphosphonic acid monomers in the second block, the first block representing between 65% and 75% by weight of the polymer, and especially 70% by weight, and the vinylphosphonic acid representing from 3% to 7% by weight of the polymer.

Preferably, the polymer comprises at least, or even consists of, isobornyl acrylate and isobornyl methacrylate monomers in a mass proportion ranging from 40/60 to 60/40 in the first block and isobutyl acrylate and vinylphosphonic acid monomers in the second block, the first block representing between 65% and 75% by weight of the polymer, and especially 70% by weight, and the vinylphosphonic acid representing from 3% to 7% by weight of the polymer.

Preferably, the polymer comprises at least, or even consists of, isobornyl acrylate and isobornyl methacrylate monomers in a mass proportion ranging from 45/55 to 55/45 in the first block and isobutyl acrylate and vinylphosphonic acid monomers in the second block, the first block representing between 65% and 75% by weight of the polymer, and especially 70% by weight, and the vinylphosphonic acid representing from 3% to 7% by weight of the polymer.

Intermediate Segment

Said first and second blocks of the polymer may be advantageously linked together via an intermediate segment comprising at least one constituent monomer of the first block and at least one constituent monomer of the second block.

The intermediate segment is a block comprising at least one constituent monomer of the first block and at least one constituent monomer of the second block of the polymer, which enables these blocks to be "compatibilized".

Advantageously, the intermediate segment comprising at least one constituent monomer of the first block and at least one constituent monomer of the second block of the polymer is a statistical polymer.

Preferably, the intermediate segment is derived essentially from constituent monomers of the first block and of the second block.

The term "essentially" means at least 85%, preferably at least 90%, better still 95% and even better still 100%.

Advantageously, the intermediate block has a glass transition temperature Tg that is between the glass transition temperatures of the first and second blocks.

The block polymer used according to the invention is advantageously a film-forming polymer. The term "film-forming polymer" means a polymer that is capable of forming, by itself or in the presence of a film-forming auxiliary agent, a continuous film that adheres to a support, especially to keratin materials.

The polydispersity index of the block polymer is advantageously greater than 2. The polydispersity index I of the polymer is equal to the ratio of the weight-average mass Mw to the number-average mass Mn.

The weight-average molar mass (Mw) and number-average molar mass (Mn) are determined by gel permeation liquid chromatography (THF solvent, calibration curve established with linear polystyrene standards, refractometric detector).

The weight-average mass (Mw) of the block polymer is preferably less than or equal to 300 000; it ranges, for example, from 35 000 to 200 000 and better still from 45 000 to 150 000 g/mol.

The number-average mass (Mn) of the block polymer is preferably less than or equal to 70 000; it ranges, for example, from 10 000 to 60 000 and better still from 12 000 to 50 000 g/mol.

Preferably, the polydispersity index of the block polymer is greater than 2, for example ranging from 3 to 20, preferably greater than or equal to 4, for example ranging from 4 to 18.

The block polymer may be prepared via a process for preparing a block polymer, which consists in mixing, in the same reactor, a polymerization solvent, an initiator, a vinylphosphonic acid monomer of formula (I) as described previously, at least one (meth)acrylate monomer of formula $CH_2=C(R_1)$—$COOR_3$ in which $R_1$ represents H or a methyl radical and $R_3$ represents a linear or branched $C_1$ to $C_6$ unsubstituted alkyl group, with the exception of a tert-butyl group, at least one (meth)acrylate monomer of formula $CH_2=C(R_1)$—$COOR_2$ in which $R_1$ represents H or a methyl radical and $R_2$ represents a $C_4$ to $C_{12}$ cycloalkyl group, according to the following sequence of steps:

some of the polymerization solvent and some of the initiator are poured into the reactor, and the mixture is heated to a reaction temperature of between 60 and 120° C., said at least one (meth)acrylate monomer of formula $CH_2=C(R_1)$—$COOR_2$ is then poured in, as a first addition, and the mixture is left to react for a time T corresponding to a maximum degree of conversion of said monomers of 90%, further polymerization initiator, the vinylphosphonic acid monomer (I) and said (meth)acrylate of $CH_2=C(R_1)$—$COOR_3$ are then poured into the reactor, as a second addition, and the mixture is left to react for a time T' after which the degree of conversion of said monomers reaches a plateau, the reaction mixture is cooled to room temperature.

The term "polymerization solvent" means a solvent or a mixture of solvents. The polymerization solvent may be chosen especially from ethyl acetate, butyl acetate, 08-016 branched alkanes such as 08-016 isoalkanes, for instance isododecane, isodecane or isohexadecane, and mixtures thereof. Preferably, the polymerization solvent is isododecane.

According to another embodiment, the process for preparing a polymer consists in mixing, in the same reactor, a polymerization solvent, an initiator, a vinylphosphonic acid monomer (I) as described previously, at least one (meth)acrylate monomer of formula $CH_2=C(R_1)$—$COOR_3$ in which $R_1$ represents H or a methyl radical and $R_3$ represents a linear or branched $C_1$ to $C_6$ unsubstituted alkyl group in which $R_3$ represents a linear or branched $C_1$ to $C_{12}$ unsubstituted alkyl group, with the exception of a tert-butyl group, at least one (meth)acrylate monomer of formula $CH_2=C(R_1)—COOR_2$ in which $R_1$ represents H or a methyl radical and $R_2$ represents a $C_4$ to $C_{12}$ cycloalkyl group in which $R_2$ represents a $C_4$ to $C_{12}$ cycloalkyl group, according to the following sequence of steps:

some of the polymerization solvent and some of the initiator are poured into the reactor, and the mixture is heated to a reaction temperature of between 60 and 120° C., the vinylphosphonic acid monomer (I) and said (meth) acrylate of formula $CH_2=C(R_1)—COOR_3$ are then poured in, as a first addition, and the mixture is left to react for a time T corresponding to a maximum degree of conversion of said monomers of 90%, further polymerization initiator and said at least one (meth)acrylate monomer of formula $CH_2=C(R_1)—COOR_2$ are then poured into the reactor, as a second addition, and the mixture is left to react for a time T' after which the degree of conversion of said monomers reaches a plateau, the reaction mixture is cooled to room temperature.

The polymerization temperature is preferably between 85 and 95° C., especially about 90° C.

The reaction time after the second addition is preferably between 3 and 6 hours.

The monomers used in the context of this process, and the proportions thereof, may be those described previously.

The polymerization is especially performed in the presence of a radical initiator especially of peroxide type (for example tert-butyl peroxy-2-ethylhexanoate: Trigonox 21S; 2,5-dimethyl-2,5-di(2-ethylhexanoylperoxy)hexane: Trigonox 141; tert-butyl peroxypivalate: Trigonox 25C75 from AkzoNobel) or of azo type, for example (AIBN: azobisisobutyronitrile; V50: 2,2'-azobis(2-amidinopropane) dihydrochloride).

The phosphonic polymer as defined previously may be present in the composition according to the invention in a content ranging from 0.1% to 40% by weight, relative to the total weight of the composition derived from the extemporaneous mixing, preferably from 0.5% to 35% by weight, preferentially ranging from 1% to 30% by weight and more preferentially ranging from 10% to 30% by weight. This is the composition that is applied to the keratin materials.

Cross Linking Agents

The additional component used in the process of the invention can be a cross linking agent, specifically an amine compound chosen from polyamine compounds containing several primary amine and/or secondary amine groups or alternatively amino alkoxysilanes. It may thus be chosen from amino alkoxysilane compounds, diamine compounds and triamine compounds.

According to a first embodiment of the invention, the polyamine compound is a compound comprising from 2 to 20 carbon atoms, in particular a non-polymeric compound. The term "non-polymeric compound" means a compound which is not directly obtained via a monomer polymerization reaction.

Polyamine compounds that may be mentioned include N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis (3-aminopropylamino)ethane, N,N'-bis(3-aminopropyl)-1,3-propanediamine, ethylenediamine, 1,3-propylenediamine, 1,4-butylenediamine, lysine, cystamine, xylenediamine, tris (2-aminoethyl)amine and spermidine. Preferably, the amine compound is chosen from ethylenediamine, 1,3-propylenediamine and 1,4-butylenediamine. Preferentially, the polyamine compound is ethylenediamine.

The polyamine compound may also be chosen from amine-based polymers, especially having a weight-average molecular weight ranging from 500 to 1 000 000, preferably ranging from 500 to 500 000, and preferentially ranging from 500 to 100 000.

As amine-based polymer, use may be made of poly(($C_2$-$C_5$)alkyleneimines), and in particular polyethyleneimines and polypropyleneimines, especially poly(ethyleneimine)s (for example the product sold under the reference 46,852-3 by the company Aldrich Chemical); poly(allylamine) (for example the product sold under the reference 47,913-6 by the company Aldrich Chemical); polyvinylamines and copolymers thereof, in particular with vinylamides; mention may in particular be made of vinylamine/vinylformamide copolymers such as those sold under the name Lupamin® 9030 by the company BASF; polyamino acids bearing $NH_2$ groups, such as polylysine, for example the product sold by the company JNC Corporation (formerly Chisso); aminodextran, such as the product sold by the company CarboMer Inc; amino polyvinyl alcohol, such as the product sold by the company CarboMer Inc, acrylamidopropylamine-based copolymers; chitosans;

polydimethylsiloxanes comprising primary amine groups at the chain end or on side chains, for example aminopropyl side or end groups, for instance those of formula (A) or (B) or (C):

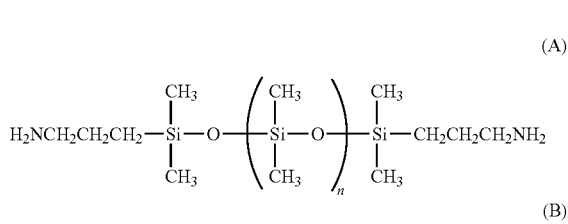

(A)

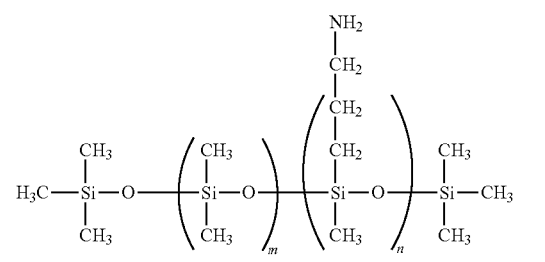

(B)

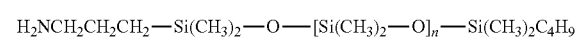

(C)

in formula (A): the value of n is such that the weight-average molecular weight of the silicone is between 500 and 55 000. As examples of aminosilicone (A), mention may be made of those sold under the names DMS-A11, DMS-A12, DMS-A15, DMS-A21, DMS-A31, DMS-A32 and DMS-A35 by the company Gelest, reference 481688 from Aldrich, in formula (B), the values of n and m are such that the weight-average molecular weight of the silicone is between 1000 and 55 000. As examples of silicone (B), mention may be made of those sold under the names AMS-132, AMS-152, AMS-162, AMS-163, AMS-191 and AMS-1203 by the company Gelest, in formula (C), the value of n is such that the weight-average molecular weight of the silicone is between 500 and 3000. As an example of silicone (C), mention may be made of those sold under the names MCR-A11 and MCR-A12 by the company Gelest;

amodimethicones of formula (D):

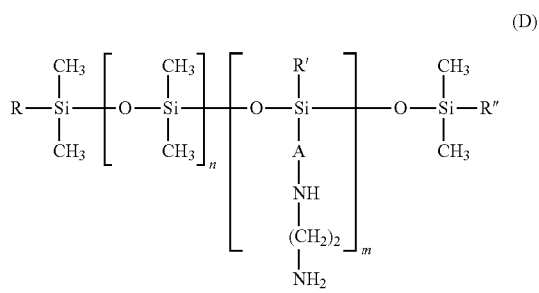

in which R, R' and R'', which may be identical or different, each represent a $C_1$-$C_4$ alkyl or hydroxyl group, A represents a O3 alkylene group and m and n are such that the weight-average molecular weight of the compound is between approximately 5000 and 500 000.

The polyether amines known especially under the reference Jeffamine from the company Huntsman; and especially:

polyethylene glycol and/or polypropylene glycol α,ω-diamines (bearing a chain-end amine function), such as those sold under the names Jeffamine D-230, D-400, D-2000, D-4000, ED-600, ED-9000, ED-2003;

polytetrahydrofuran (or polytetramethylene glycol) α,ω-diamines;

polybutadiene α,ω-diamines;

polyamidoamine (PANAM) dendrimers bearing amine end functions;

poly(meth)acrylates or poly(meth)acrylamides bearing primary or secondary amine side functions, such as poly(3-aminopropyl)methacrylamide or poly(2-aminoethyl) methacrylate.

As amine-based polymer, use is preferably made of polydimethylsiloxanes comprising primary amine groups at the chain end or on side chains.

Preferentially, polydimethylsiloxanes comprising aminopropyl end groups at the chain end are used.

Advantageously, the polyamine compounds used in the process according to the invention are chosen from ethylenediamine and polydimethylsiloxanes comprising primary amine groups at the chain end or on side chains.

The amine compound may also be chosen from amino alkoxysilanes, such as those of formula (III):

$$R'_1Si(OR'_2)_z(R'_3)_x \quad (III)$$

in which:

R'$_1$ is a linear or branched, saturated or unsaturated, cyclic or acyclic $C_1$-$C_6$ hydrocarbon-based chain substituted with a group chosen from the following groups:
  amine $NH_2$ or NHR with R=$C_1$-$C_4$ alkyl,
  an aryl or aryloxy group substituted with an amino group or with a $C_1$-$C_4$ aminoalkyl group,
R'$_1$ possibly being interrupted in its chain with a heteroatom (O, S, NH) or a carbonyl group (CO), R'1 being linked to the silicon atom directly via a carbon atom, R'$_2$ and R'$_3$, which may be identical or different, represent a linear or branched alkyl group comprising from 1 to 6 carbon atoms, z denotes an integer ranging from 1 to 3, and x denotes an integer ranging from 0 to 2, with z+x=3.

Preferably, R'$_2$ represents an alkyl group comprising from 1 to 4 carbon atoms.

Preferably, R'$_2$ represents a linear alkyl group, comprising from 1 to 4 carbon atoms.

Preferably, R'$_2$ represents an ethyl group.

Preferably, R'$_3$ represents an alkyl group comprising from 1 to 4 carbon atoms.

Preferably, R'$_3$ represents a linear alkyl group, comprising from 1 to 4 carbon atoms.

Preferably, R'$_3$ represents a methyl or ethyl group.

Preferably, R'$_1$ is an acyclic chain.

Preferably, R'$_1$ is a linear or branched, saturated or unsaturated $C_1$-$C_6$ hydrocarbon-based chain, substituted with an amine group $NH_2$ or NHR (R=$C_1$-$C_6$ alkyl, $C_3$-$C_6$ cycloalkyl or $C_6$ aromatic). Preferentially, R'$_1$ is a saturated linear $C_1$-$C_6$ hydrocarbon-based chain substituted with an amine group $NH_2$. More preferentially, R'$_1$ is a saturated linear $C_2$-$C_4$ hydrocarbon-based chain substituted with an amine group $NH_2$.

Preferably, R'$_1$ is a saturated linear $C_1$-$C_6$ hydrocarbon-based chain substituted with an amine group $NH_2$, R'$_2$ represents an alkyl group comprising from 1 to 4 carbon atoms, R'$_3$ represents an alkyl group comprising from 1 to 4 carbon atoms.

Preferably, z is equal to 3.

Preferably, the aminosilane of formula (III) is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl) phenethyltrimethoxysilane.

Preferably, the aminosilane (III) is chosen from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane.

Preferably, the aminosilane (III) is 3-aminopropyltriethoxysilane (APTES).

Preferably, the amine compound is chosen from 3-aminopropyltriethoxysilane (APTES), N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl) aminopropylamine, bis(3-aminopropyl)amine, methylbis(3-aminopropyl)amine, N-(3-aminopropyl)-1,4-diaminobutane, N,N-dimethyldipropylenetriamine, 1,2-bis (3-aminopropylamino)ethane, N,N'-bis(3-aminopropyl)-1, 3-propanediamine, ethylenediamine and lysine.

Preferentially, the amine compounds used in the process according to the invention are chosen from polydimethylsiloxanes comprising primary amine groups at the chain end or on side chains, 3-aminopropyltriethoxysilane (APTES). More preferentially, polydimethylsiloxanes comprising aminopropyl end groups at the chain end, 3-aminopropyltriethoxysilane (APTES), are used.

Advantageously, the amine compound used in the process according to the invention is used in a mole ratio of amine group of the amine compound/phosphonic acid group of the phosphonic polymer ranging from 0.01 to 10, preferably ranging from 0.1 to 5, preferentially ranging from 0.1 to 2 and more preferentially ranging from 0.1 to 1.

On contact with the phosphonic polymer, the polyamine compound reacts with the phosphonic acid functions to form a crosslinked polymer, for example in the following manner:

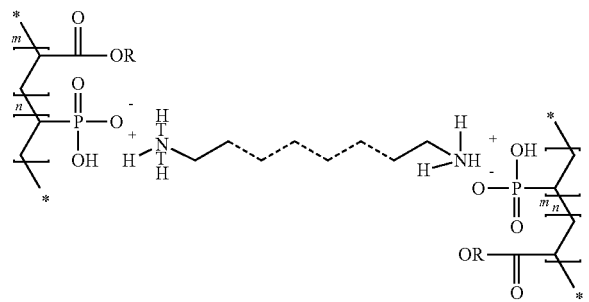

Scheme I

The crosslinked polymer may thus be obtained by reacting said polyamine compound with the vinylphosphonic acid block polymer described previously. Some or all of the anhydride groups react with the NH or $NH_2$ group of the polyamine compound and form a unit bearing an amide group and a carboxylic acid group as described in scheme I.

On contact with the phosphonic polymer, in anhydrous medium, the amino alkoxysilane compound (II) reacts with the phosphonic acid functions to form a unit having the following formula:

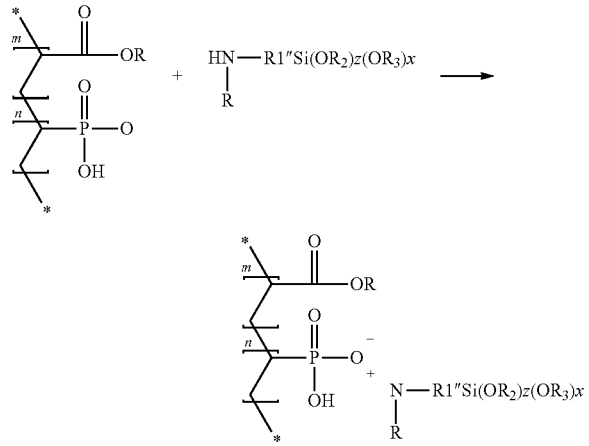

Scheme II

Such a block polymer bearing an amino alkoxysilane group obtained by reacting the phosphonic block polymer with the amino alkoxysilane compound (II) is novel and thus also forms the subject of the present invention. A subject of the invention is also an anhydrous composition comprising such a block polymer bearing an amino alkoxysilane group and a physiologically acceptable medium.

Pigments

The composition that is useful in the process of the invention comprises at least one pigment. The term "pigment" means any pigment that gives colour to keratin materials. Their solubility in water at 25° C. and at atmospheric pressure (760 mmHg) is less than 0.05% by weight, and preferably less than 0.01%.

The pigments that may be used are especially chosen from the organic and/or mineral pigments known in the art, especially those described in Kirk-Othmer's *Encyclopaedia of Chemical Technology* and in Ullmann's *Encyclopaedia of Industrial Chemistry*.

These pigments may be in pigment powder or paste form. They may be coated or uncoated. The pigments may be chosen, for example, from mineral pigments, organic pigments, lakes, pigments with special effects, such as nacres or glitter flakes, and mixtures thereof.

The pigment may be a mineral pigment. The term "mineral pigment" means any pigment that satisfies the definition in Ullmann's encyclopaedia in the chapter on inorganic pigments. Among the mineral pigments that are useful in the present invention, mention may be made of iron oxides, chromium oxides, manganese violet, ultramarine blue, chromium hydrate, ferric blue and titanium oxide.

The pigment may be an organic pigment. The term "organic pigment" means any pigment that satisfies the definition in Ullmann's encyclopaedia in the chapter on organic pigments. The organic pigment may in particular be chosen from nitroso, nitro, azo, xanthene, quinoline, anthraquinone, phthalocyanin, metal complex type, isoindolinone, isoindoline, quinacridone, perinone, perylene, diketopyrrolopyrrole, thioindigo, dioxazine, triphenylmethane and quinophthalone compounds.

In particular, the white or coloured organic pigments may be chosen from carmine, carbon black, aniline black, azo yellow, quinacridone, phthalocyanin blue, sorghum red, the blue pigments codified in the Color Index under the references CI 42090, 69800, 69825, 73000, 74100, 74160, the yellow pigments codified in the Color Index under the references CI 11680, 11710, 15985, 19140, 20040, 21100, 21108, 47000, 47005, the green pigments codified in the Color Index under the references CI 61565, 61570, 74260, the orange pigments codified in the Color Index under the references CI 11725, 15510, 45370, 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, 75470, the pigments obtained by oxidative polymerization of indole or phenolic derivatives as described in patent FR 2 679 771.

The pigments in accordance with the invention may also be in the form of composite pigments, as described in patent EP 1 184 426. These composite pigments may be composed especially of particles comprising a mineral core, at least one binder, which provides for the attachment of the organic pigments to the core, and at least one organic pigment which at least partially covers the core.

The organic pigment may also be a lake. The term "lake" means dyes adsorbed onto insoluble particles, the assembly thus obtained remaining insoluble during use.

The mineral substrates onto which the dyes are adsorbed are, for example, alumina, silica, calcium sodium borosilicate or calcium aluminium borosilicate and aluminium.

Among the dyes, mention may be made of cochineal carmine. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), D&C Blue 1 (CI 42 090).

Mention may be made, as examples of lakes, of the product known under the following name: D&C Red 7 (CI 15 850:1).

The pigment may also be a pigment with special effects. The term "pigments with special effects" means pigments that generally create a coloured appearance (characterized by a certain shade, a certain vivacity and a certain level of luminance) that is non-uniform and that changes as a function of the conditions of observation (light, temperature, angles of observation, etc.). They thus contrast with coloured pigments that afford a standard uniform opaque, semi-transparent or transparent shade.

Several types of pigments with special effects exist: those with a low refractive index, such as fluorescent, photochromic or thermochromic pigments, and those with a higher refractive index, such as nacres or glitter flakes.

Examples of pigments with special effects that may be mentioned include nacreous pigments such as titanium mica coated with an iron oxide, mica coated with an iron oxide, mica coated with bismuth oxychloride, titanium mica coated with chromium oxide, titanium mica coated with an organic dye especially of the abovementioned type, and also nacreous pigments based on bismuth oxychloride. They may also be mica particles, at the surface of which are superposed at least two successive layers of metal oxides and/or of organic dyestuffs.

The nacres may more particularly have a yellow, pink, red, bronze, orangey, brown, gold and/or coppery colour or tint.

As illustrations of nacres that may be used in the context of the present invention, mention may be made of gold-coloured nacres sold especially by the company Engelhard under the name Gold 222C (Cloisonne), Sparkle gold (Timica), Gold 4504 (Chromalite) and Monarch gold 233X (Cloisonne); the bronze nacres sold especially by the company Merck under the names Bronze fine (17384) (Colorona) and Bronze (17353) (Colorona), by the company Eckart under the name Prestige Bronze and by the company Engelhard under the name Super bronze (Cloisonne); the orange nacres sold especially by the company Engelhard under the names Orange 363C (Cloisonne) and Orange MCR 101 (Cosmica) and by the company Merck under the names Passion orange (Colorona) and Matte orange (17449) (Microna); the brown-tinted nacres sold especially by the company Engelhard under the names Nuantique copper 340X6 (Cloisonne) and Brown CL4509 (Chromalite); the nacres with a copper tint sold especially by the company Engelhard under the name Copper 340A (Timica) and by the company Eckart under the name Prestige Copper; the nacres with a red tint sold especially by the company Merck under the name Sienna fine (17386) (Colorona); the nacres with a yellow tint sold especially by the company Engelhard under the name Yellow (4502) (Chromalite); the red-tinted nacres with a golden tint sold especially by the company Engelhard under the name Sunstone G012 (Gemtone); the black nacres with a golden tint sold especially by the company Engelhard under the name Nu antique bronze 240 AB (Timica); the blue nacres sold especially by the company Merck under the name Matte blue (17433) (Microna), Dark Blue (117324) (Colorona); the white nacres with a silvery tint sold especially by the company Merck under the name Xirona Silver; and the golden-green pinkish-orange nacres sold especially by the company Merck under the name Indian summer (Xirona), and mixtures thereof.

In addition to nacres on a mica support, multilayer pigments based on synthetic substrates such as alumina, silica, sodium calcium borosilicate or calcium aluminium borosilicate, and aluminium, may be envisaged.

Mention may also be made of pigments with an interference effect which are not attached to a substrate, such as liquid crystals (Helicones HC from Wacker) or interference holographic glitter (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

The variety of pigments that may be used in the present invention makes it possible to obtain a wide range of colours, and also particular optical effects such as metallic effects or interference effects.

The size of the pigment used in the cosmetic composition according to the present invention is generally between 10 nm and 200 µm, preferably between 20 nm and 80 µm and even more preferably between 30 nm and 50 µm.

The pigments may be dispersed in the product by means of a dispersant.

The dispersant serves to protect the dispersed particles against their agglomeration or flocculation. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. In particular, 12-hydroxystearic acid esters and $C_8$ to $C_{20}$ fatty acid esters of polyols such as glycerol or diglycerol are used, such as poly(12-hydroxystearic acid) stearate with a molecular weight of about 750 g/mol, such as the product sold under the name Solsperse 21 000 by the company Avecia, polyglyceryl-2 dipolyhydroxystearate (CTFA name) sold under the reference Dehymyls PGPH by the company Henkel, or poly-hydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the cosmetic composition according to the invention may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described especially in Cosmetics and Toiletries, February 1990, Vol. 105, pp. 53-64, before being dispersed in the composition in accordance with the invention. These organic agents may be chosen, for example, from amino acids; waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides;

polysaccharides, for example chitosan, cellulose and derivatives thereof; polyethylene; (meth)acrylic polymers, for example polymethyl methacrylates; polymers and copolymers containing acrylate units; proteins; alkanolamines; silicone compounds, for example silicones, polydimethylsiloxanes, alkoxysilanes, alkylsilanes and siloxysilicates; organofluorine compounds, for example perfluoroalkyl ethers; fluorosilicone compounds.

The surface-treated pigments that are useful in the cosmetic composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available in the required form.

Preferably, the surface-treated pigments are coated with an organic layer.

The organic agent with which the pigments are treated may be deposited on the pigments by evaporation of solvent, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is especially described in patent U.S. Pat. No. 4,578,266.

An organic agent covalently bonded to the pigments will preferably be used.

The agent for the surface treatment may represent from 0.1% to 50% by weight, preferably from 0.5% to 30% by weight and even more preferentially from 1% to 10% by weight relative to the total weight of the surface-treated pigments.

Preferably, the surface treatments of the pigments are chosen from the following treatments:
  a PEG-silicone treatment, for instance the AQ surface treatment sold by LCW;
  a chitosan treatment, for instance the CTS surface treatment sold by LCW;
  a triethoxycaprylylsilane treatment, for instance the AS surface treatment sold by LCW;
  a methicone treatment, for instance the SI surface treatment sold by LCW;
  a dimethicone treatment, for instance the Covasil 3.05 surface treatment sold by LCW;
  a dimethicone/trimethyl siloxysilicate treatment, for instance the Covasil 4.05 surface treatment sold by LCW;
  a lauroyllysine treatment, for instance the LL surface treatment sold by LCW;
  a lauroyllysine dimethicone treatment, for instance the LL/SI surface treatment sold by LCW;
  a magnesium myristate treatment, for instance the MM surface treatment sold by LCW;
  an aluminium dimyristate treatment, such as the MI surface treatment sold by Miyoshi;
  a perfluoropolymethylisopropyl ether treatment, for instance the FHC surface treatment sold by LCW;
  an isostearyl sebacate treatment, for instance the HS surface treatment sold by Miyoshi;
  a disodium stearoyl glutamate treatment, for instance the NAI surface treatment sold by Miyoshi;
  a dimethicone/disodium stearoyl glutamate treatment, for instance the SA/NAI surface treatment sold by Miyoshi;
  a perfluoroalkyl phosphate treatment, for instance the PF surface treatment sold by Daito;
  an acrylate/dimethicone copolymer and perfluoroalkyl phosphate treatment, for instance the FSA surface treatment sold by Daito;
  a polymethylhydrogenosiloxane/perfluoroalkyl phosphate treatment, for instance the FS01 surface treatment sold by Daito;
  a lauroyllysine/aluminium tristearate treatment, for instance the LL-StAI surface treatment sold by Daito;
  an octyltriethylsilane treatment, for instance the OTS surface treatment sold by Daito;
  an octyltriethylsilane/perfluoroalkyl phosphate treatment, for instance the FOTS surface treatment sold by Daito;
  an acrylate/dimethicone copolymer treatment, for instance the ASC surface treatment sold by Daito;
  an isopropyl titanium triisostearate treatment, for instance the ITT surface treatment sold by Daito;
  a microcrystalline cellulose and carboxymethylcellulose treatment, for instance the AC surface treatment sold by Daito;
  a cellulose treatment, for instance the C2 surface treatment sold by Daito;
  an acrylate copolymer treatment, for instance the APD surface treatment sold by Daito;
  a perfluoroalkyl phosphate/isopropyl titanium triisostearate treatment, for instance the PF+ITT surface treatment sold by Daito.

The composition in accordance with the present invention may furthermore comprise one or more surface-untreated pigments.

According to a particular embodiment of the invention, the pigment(s) are mineral pigments.

According to another particular embodiment of the invention, the pigment(s) are chosen from nacres.

The amount of pigments may range from 0.5% to 40% and preferably from 1% to 20%.

Hydrocarbon-Based Oil

According to a preferred embodiment of the invention, the composition comprising the phosphonic polymer may contain a hydrocarbon-based oil.

The hydrocarbon-based oil is an oil that is liquid at room temperature (25° C.).

The term "hydrocarbon-based oil" means an oil formed essentially from, or even constituted of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be volatile or non-volatile.

The hydrocarbon-based oil may be chosen from:
  hydrocarbon-based oils containing from 8 to 14 carbon atoms, and especially:
    branched $C_8$-$C_{14}$ alkanes, for instance $C_8$-$C_{14}$ isoalkanes of petroleum origin (also known as isoparaffins), for instance isododecane (also known as 2,2,4,4,6-pentamethylheptane), isodecane and isohexadecane, for example, the oils sold under the trade names Isopar or Permethyl,
  linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in examples 1 and 2 of patent application WO 2008/155 059 from the company Cognis, and mixtures thereof, short-chain esters (containing from 3 to 8 carbon atoms in total) such as ethyl acetate, methyl acetate, propyl acetate or n-butyl acetate, hydrocarbon-based oils of plant origin such as triglycerides constituted of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812° and 818° by the company Dynamit Nobel, synthetic ethers containing from 10 to 40 carbon atoms;

linear or branched hydrocarbons of mineral or synthetic origin, such as petroleum jelly, polydecenes, hydrogenated polyisobutene such as Parleam®, squalane and liquid paraffins, and mixtures thereof, synthetic esters such as oils of formula $R_1COOR_2$ in which $R_1$ represents a linear or branched fatty acid residue containing from 1 to 40 carbon atoms and $R_2$ represents an, in particular branched, hydrocarbon-based chain containing from 1 to 40 carbon atoms, on the condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Advantageously, the hydrocarbon-based oil is apolar (thus formed solely from carbon and hydrogen atoms).

The hydrocarbon-based oil is preferably chosen from hydrocarbon-based oils containing from 8 to 14 carbon atoms, in particular the apolar oils described previously.

Preferentially, the hydrocarbon-based oil is isododecane.

Silicone Oil

The composition comprising the polymer may contain, in addition to the hydrocarbon-based oil, a silicone oil. The term "silicone oil" means an oil comprising at least one silicon atom and especially at least one Si—O group. The silicone oil may be volatile or non-volatile.

The term "volatile oil" means an oil (or non-aqueous medium) that is capable of evaporating on contact with the skin in less than one hour, at room temperature and at atmospheric pressure. The volatile oil is a volatile cosmetic oil, which is liquid at room temperature, especially having a non-zero vapour pressure, at room temperature and at atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

The term "non-volatile oil" means an oil with a vapour pressure of less than 0.13 Pa.

Volatile silicone oils that may be mentioned include volatile linear or cyclic silicone oils, especially those with a viscosity ≤8 centistokes (cSt) ($8\times10^{-6}$ m$^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made in particular of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of linear or cyclic non-volatile polydimethylsiloxanes (PDMSs); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

Advantageously, the composition may comprise a hydrocarbon-based oil in a content ranging from 60% to 100% by weight relative to the total weight of the oils present in the composition and from 0 to 40% by weight of silicone oil. According to a preferred embodiment of the invention, the composition contains as oil only a hydrocarbon-based oil.

Plasticizers

The composition can comprises a plasticizer. Such a plasticizier can be chosen from tri-n-butyl citrate, tripropylene glycol monomethyl ether (INCI name: PPG-3 methyl ether) and trimethyl pentaphenyl trisiloxane (sold under the name Dow Corning PH-1555 HRI Cosmetic Fluid by the company Dow Corning). These plasticizers make it possible to improve the mechanical strength of the polymer film.

The plasticizer may be present in an amount ranging from 5% to 50% by weight, relative to the total weight of the polymer of the particles.

For plasticizing the polymer, non volatile oil can be used. These oils, non volatile, remains in the polymer thus rendering it soft. Non-volatile hydrocarbonated or siliconated oils above described can be used as plasticizer. Preferred oils are alkane oils linear or branched, ester such as synthetic ester oil described above.

According to a preferred embodiment, the process of the invention is carried out with a plasticizers and a crosslinking agent, more preferably the process is carried out with an aminosiloxane and a non-volatile hydrocarbonated oil such as isohexadecane, isononyl isonanoate.

Other particular additional components may be used in the process according to the invention to contribute towards improving the film-forming properties of the polymer according to the invention. Such additional components are especially the salts of divalent or trivalent metal ions, clays and metal oxides described below.

The composition according to the invention may comprise salts of divalent or trivalent metal ions, chosen in particular from salts of ions derived from Al(III), Ca(II), Cu(II), Fe(II), Fe(III), Mg(II), Mn(II), Zn(II), and mixtures thereof. Ions derived from Ca(II), Mg(II) are preferred. The salts of these metal ions are well known, with, for example, anions such as gluconate, chloride, sulfate, hydroxide, acetate and stearate. For example, use may be made of the following salts: calcium gluconate, calcium chloride, magnesium chloride, copper chloride, magnesium gluconate, iron sulfate, iron gluconate, aluminium sulfate, sodium stearate.

Said salts of divalent or trivalent metal ions may be present in the composition according to the invention in a content ranging from 0.1% to 20% by weight, preferably from 0.1% to 15% by weight, relative to the total weight of the composition.

Alternatively, the salt of divalent or trivalent metal ions may be applied sequentially in the process according to the invention.

The composition according to the invention may comprise a clay.

Clays are products that are already well known per se, which are described, for example, in the publication Minéralogie des argiles [Mineralogy of Clays], S. Caillère, S. Hénin, M. Rautureau, 2nd Edition 1982, Masson, the teaching of which is included herein by way of reference.

Among the clays, examples that may be mentioned include clays of the smectite family, such as laponite and montmorillonite, of the kaolinite family, such as kaolinite, dickite, nacrite, optionally modified clays of the halloysite, dombassite, antigorite, benthierine, pyrophyllite, montmorillonite, beidellite, vermiculite, talc, stevensite, hectorite, bentonite, saponite, chlorite, sepiolite and illite family.

The clay(s) present in the composition of the invention may be natural or synthetic. Natural clay is a sedimentary rock composed to a large extent of specific minerals, silicates generally of aluminium. Kaolin is thus a natural clay.

The clays may also be chemically modified with various compounds, such as acrylic acids, polysaccharides (for example carboxymethylcellulose) or organic cations.

Preferably, in the context of the present invention, use is made of clays that are cosmetically compatible with and acceptable for the skin and/or the scalp.

According to a particular embodiment of the present invention, the clay used is chosen from kaolinite, montmorillonites, saponites, laponites, bentonites, and in particular hectorites, and illites. Use is even more particularly made of mixtures of clays, and natural clays.

Natural clays that may be mentioned include green clays, in particular rich in illite; clays rich in montmorillonite, known as fuller's earth, or such as bentonite or else white clays rich in kaolinite. Bentonites that may be mentioned in particular include those sold under the names Bentone 38 VCG, Bentone Gel CAO V, Bentone 27 V, Bentone Gel MIO V and Bentone Gel ISD V by the company Elementis.

Montmorillonites and smectites are hydrated aluminium and/or magnesium silicates. Examples that may be mentioned include the montmorillonite sold under the name Gel White H by the company Rockwood Additives, and the purified smectite sold under the name Veegum Granules by the company Vanderbilt. Mention may also be made of the montmorillonite sold under the name Kunipia G4 by the company Kunimine and the sepiolite Pangel S9 sold by the company Tolsa.

Examples of kaolinites that may be mentioned include the kaolins sold under the name Coslin C 100 by the company BASF Personal Care Ingredients or Kaolin Supreme by the company Imerys.

Talcs are hydrated magnesium silicates usually comprising aluminium silicate. The crystal structure of talc consists of repeated layers of a sandwich of brucite between layers of silica. Examples that may be mentioned include micronized magnesium silicate of particle size 5 microns sold under the name Micro Ace P3 by the company Nippon Talc or the talcs sold under the names Rose Talc and Talc SG-2000 by the company Nippon Talc, J 68 BC by the company US Cosmetics (Miyoshi), Lyzenac 00 and Luzenac Pharma M by the company Luzenac, and Talc JA-46R by the company Asada Milling.

As saponite, which belongs to the montmorillonite family, mention may be made of synthetic saponite, in particular the product sold by the company Kunimine under the name Sumecton®.

An example of a synthetic laponite that may be mentioned is the laponite XLG sold by the company Rockwood.

The clay may be present in the composition according to the invention in an amount ranging from 0.1% to 50% by weight, especially from 1% to 30% by weight and in particular from 1% to 20% by weight relative to the total weight of the composition.

The metal oxides may be chosen from titanium dioxide, iron oxides, zirconium oxides, zinc oxides, cerium oxides and chromium oxides. Iron oxides or titanium dioxide are preferably used.

The metal oxide may be present in the composition according to the invention in an amount ranging from 0.1% to 50% by weight, especially from 1% to 30% by weight and in particular from 1% to 20% by weight relative to the total weight of the composition.

The composition according to the invention may comprise a cosmetic additive chosen from fragrances, preserving agents, fillers, UV-screening agents, oils, waxes, surfactants, moisturizers, vitamins, ceramides, antioxidants, free-radical scavengers, polymers, thickeners and dyestuffs.

The composition according to the invention may also comprise other dyestuffs, such as liposoluble dyes or water-soluble dyes. This dyestuff may be present in a content ranging from 0.01% to 30% by weight, relative to the total weight of the composition.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes are, for example, beetroot juice or methylene blue.

According to one embodiment, the composition used according to the invention is an anhydrous composition. The term "anhydrous composition" means a composition containing less than 2% by weight of water, or even less than 0.5% of water, and is especially free of water. Where appropriate, such small amounts of water may especially be introduced by ingredients of the composition that may contain residual amounts thereof. In particular, when the amine compound is an amino alkoxysilane (III) as defined previously, the composition containing it and the compositions used in the process are anhydrous compositions. Advantageously, these compositions also contain a $C_2$-$C_5$ monoalcohol such as ethanol or isopropanol, especially in a content ranging from 0.1% to 5% by weight, relative to the total weight of the composition.

The invention will now be described with reference to the examples that follow, which are given as non-limiting illustrations.

EXAMPLE 1: ISOBORNYL METHACRYLATE/ISOBORNYL ACRYLATE (35/35)-CO-ISOBUTYL ACRYLATE/VINYLPHOSPHONIC ACID (25/5) COPOLYMER (COPOLYMER 1)

150 g of isododecane were placed in a 1 litre reactor and the solvent was then heated, increasing the temperature from 25° C. to 90° C. over 1 hour.

105 g of isobornyl methacrylate, 105 g of isobornyl acrylate and 1.8 g of initiator 2,5-bis(2-ethylhexanoylperoxy)-2,5-dimethylhexane (Trigonox® 141 from AkzoNobel) were then added over 1 hour, while maintaining the temperature at 90° C. The mixture was maintained at 90° C. for 1 hour 30 minutes.

75 g of isobutyl acrylate, 15 g of vinylphosphonic acid, 1.2 g of 2,5-bis(2-ethylhexanoylperoxy)-2,5-dimethylhexane and 20 g of ethanol were then added over 30 minutes, still at 90° C.

The mixture was maintained at 90° C. for 3 hours and was then diluted with 150 g of isododecane, and then concentrated by distillation to remove the unreacted monomers.

A solution containing 50% by weight of the polymer in isododecane was finally obtained.

The polymer obtained has a number-average molecular weight (Mn) of 20 800 and a weight-average molecular weight (Mw) of 3 122 000; with an Ip=15.

Preparation of the Dyeing Compositions
Comparison 1:
A dyeing composition was prepared from the solution of example 1 containing the copolymer 1 as above described (15% active material in isododecane), 6% of pigment (MICA (and) IRON OXIDES) and qs to 100% with isododecane.
Invention 1:
A dyeing composition was prepared from the solution of example 1 containing the copolymer 1 as above described (15% active material in isododecane), 6% of pigment (MICA (and) IRON OXIDES), 3% of tributylcitrate (plasticizer) and qs to 100% with isododecane.
Invention 2:
A dyeing composition was prepared from the solution of example 1 containing the copolymer 1 as above described (15% active material in isododecane), 6% of pigment (MICA (and) IRON OXIDES), 3% of isohexadecane (plasticizing non volatile oil) and qs to 100% with isododecane.
Invention 3:
A dyeing composition was prepared from the solution of example 1 containing the copolymer 1 as above described (15% active material in isododecane), 6% of pigment (MICA (and) IRON OXIDES), 3% of isononyle isonanoate (plasticizing non volatile oil) and qs to 100% with isododecane.
Invention 4:
A dyeing composition was prepared from the solution of example 1 containing the copolymer 1 as above described (7.5% active material in isododecane), 6% of pigment (MICA (and) IRON OXIDES), 7.5% of (3-aminopropyl) triethoxysilane APTES (crosslinking agent) and qs to 100% with isododecane.
Invention 5:
A dyeing composition was prepared from the solution of example 1 containing the copolymer 1 as above described (15% active material in isododecane), 6% of pigment (MICA (and) IRON OXIDES), 3% of poly(dimethylsiloxane), bis(3-aminopropyl) terminated with Mn 25000 g/mol (PDMS-diNH2) and qs to 100% with isododecane.
Invention 6:
A dyeing composition was prepared from the solution of example 1 containing the copolymer 1 as above described (7.5% active material in isododecane), 6% of pigment (MICA (and) IRON OXIDES), 7.5% of APTES, 3% of Tributylcitrate and qs to 100% with isododecane.
Comparison 2:
A comparative composition was prepared from a solution of a pseudo block ACRYLIC ACID/ISOBUTYL ACRYLATE/ISOBORNYL ACRYLATE COPOLYMER 50% in isododecane (15% active material), 6% of pigment (MICA (and) IRON OXIDES) and qs 100% isododecane.

Evaluation of the Color Resistance
These dyeing compositions were applied on locks of natural hair with 90% of white hair. The compositions were applied on dried hair and on wet hair. 0.5 g of the dyeing composition was applied on 1 g of hair lock. After 24 h hours, the locks were washed and dried. Then, the locks were evaluated on dried hair after 1 shampoo, after 3 shampoos and then after 5 shampoos.

The color resistance was visually evaluated on dried hair after 1 shampoo, 3 shampoos and 5 shampoos according to a resistance evaluation scale ranging from 5 (high color resistance) to 1 (no color resistance).

After water rinsing and after 1, 3 and 5 shampoos, the color resistance was visually evaluated according to a color resistance evaluation scale ranging from 5 (high color resistance) to 1 (no color resistance).

| | Application on | Water resistance | After 1 shampoo | After 3 shampoo | After 5 shampoo |
| --- | --- | --- | --- | --- | --- |
| Comparison 1 | Dried hair | 5 | 1 | 1 | 1 |
| Comparison 2 | Dried hair | 5 | 1 | 1 | 1 |
| Invention 1 (tributyl citrate) | Dried hair | 5 | 2 | 1 | 1 |
| Invention 2 (isohexadecane) | Dried hair | 5 | 2 | 1 | 1 |
| Invention 3 (isononyl isonanoate) | Dried hair | 5 | 4 | 1 | 1 |
| Invention 4 (APTES) | Dried hair | 5 | 4 | 1 | 1 |
| Invention 5 ((PDMS – diNH2) | Dried hair | 5 | 2 | 1 | 1 |
| Invention 6 (APTES + Tributyl citrate) | Dried Hair | 5 | 5 | 3 | 1 |

These examples show that the composition of the invention provides an improvement of the color resistance to shampoos. After 5 shampoos, the color is still acceptable.

The invention claimed is:
1. A hair dyeing process comprising the application on hair of (i) at least one pigment,
(ii) at least one block polymer comprising:
at least one first block with a glass transition temperature (Tg) of greater than or equal to 40° C. and obtained from at least one (meth)acrylate monomer of formula $CH_2=C(R_1)-COOR_2$ in which $R_1$ represents H or a methyl radical and $R_2$ represents a $C_4$ to $C_{12}$ cycloalkyl group; and at least one second block with a glass transition temperature (Tg) of less than or equal to 20° C. and is obtained from at least one vinylphosphonic acid monomer of formula (I) and from at least one (meth)acrylate monomer of formula CH$_2$═C(R$_1$)—COOR$_3$ in which R$_1$ represents H or a methyl radical and R$_3$ represents either a linear or branched C$_1$ to C$_6$ unsubstituted alkyl group, with the exception of a tert-butyl group or a methoxyethyl group;

said vinylphosphonic acid monomer of formula (I) being:

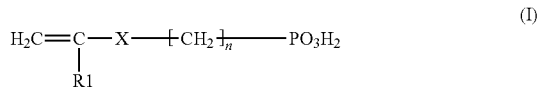

in which:
R1 denotes H or CH$_3$;
X denotes a covalent bond and n denotes an integer ranging from 0 to 14;
or X denotes a —COO— group and n denotes an integer ranging from 2 to 6, and
(iii) at least one additional compound selected from plasticizers and/or crosslinking agents.

2. The process according to claim 1, wherein the first block is obtained from at least one acrylate monomer of formula CH$_2$═CH—COOR$_2$ in which R$_2$ represents a C$_4$ to C$_{12}$ cycloalkyl group, and from at least one methacrylate monomer of formula CH$_2$═C(CH$_3$)—COOR'$_2$ in which R'$_2$ represents a C$_4$ to C$_{12}$ cycloalkyl group;
and optionally an additional monomer chosen from linear or branched C$_8$-C$_{22}$ alkyl (meth)acrylates.

3. The process according to claim 2, wherein, for the first block, said acrylate monomer and said methacrylate monomer are in acrylate/methacrylate mass proportions of between 30/70 and 70/30.

4. The process according to claim 3, wherein the first block is obtained by polymerization of isobornyl methacrylate and isobornyl acrylate.

5. The process according to claim 1, wherein the proportion of the first block ranges from 60% to 80% by weight of the polymer.

6. The process according to claim 1, wherein, for the monomer of formula (I):
X denotes a covalent bond and n is an integer ranging from 0 to 6 or X denotes a —COO— group and n is an integer ranging from 2 to 4.

7. The process according to claim 1, wherein, for monomer of formula (I), R1═H and X denotes a covalent bond and n is an integer ranging from 0 to 4.

8. The process according to claim 1, wherein monomer of formula (I) is selected from the group consisting of:
vinylphosphonic acid;
3-butenylphosphonic acid;
4-pentenylphosphonic acid;
10-undecenylphosphonic acid;
11-dodecenylphosphonic acid;
2-phosphonoethyl ester of 2-methyl-2-propenoic acid; and
2-phosphonoethyl ester of 2-propenoic acid.

9. The process according to claim 1, wherein the second block comprises a monomer selected from the group consisting of isobutyl acrylate, ethyl acrylate, n-butyl acrylate and methoxyethyl acrylate, and mixtures thereof.

10. The process according to claim 1, wherein, for the second block, the vinylphosphonic acid monomer of formula (I) and said (meth)acrylate monomer are in (meth)acrylate/vinylphosphonic acid monomer of formula (I) mass proportions ranging from 1 to 10.

11. The process according to claim 1, wherein the proportion of the second block ranges from 20% to 40% by weight of the polymer.

12. The process according to claim 1, wherein the at least one block polymer comprises an intermediate segment comprising at least one constituent monomer of the first block and at least one constituent monomer of the second block.

13. The process according to claim 1, wherein the at least one block polymer has a polydispersity index of greater than 2.

14. The process according to claim 1 in which a composition comprising the at least one pigment, the at least one block polymer, and the at least one additional compound is applied to the hair and the amount of pigment in the composition applied to the hair is between 0.5% and 40% by weight relative to the total weight of the composition.

15. The process according to claim 1, wherein a composition comprising the at least one pigment, the at least one block polymer, and the at least one additional compound is applied to the hair and the additional compound is a crosslinking agent is
an amine compound chosen from polyamine compounds bearing several primary amine groups and/or secondary amine groups and amino alkoxysilanes,
the composition being anhydrous when the crosslinking agent is an amino alkoxysilane.

16. The process according to claim 15, wherein the amine compound comprises from 2 to 20 carbon atoms.

17. The process according to claim 15, wherein the amine compound is selected from the group consisting of N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine, lysine, cystamine, xylenediamine, tris(2-aminoethyl)amine and spermidine.

18. The process according to claim 15, wherein the crosslinking agent is an amino alkoxysilane and the amino alkoxysilane is of formula (III):

in which:
R'$_1$ is a linear or branched, saturated or unsaturated, cyclic or acyclic C$_1$-C$_6$ hydrocarbon-based chain substituted with a group selected from the group consisting of the following groups:
amine NH$_2$ or NHR with R═C$_1$-C$_4$ alkyl,
an aryl or aryloxy group substituted with an amino group or with a C$_1$-C$_4$ aminoalkyl group,
R'$_1$ possibly being interrupted in its chain with a heteroatom or a carbonyl group, R'$_1$ being linked to the silicon atom directly via a carbon atom,
R'$_2$ and R'$_3$, which may be identical or different, represent a linear or branched alkyl group comprising from 1 to 6 carbon atoms,
z denotes an integer ranging from 1 to 3, and
x denotes an integer ranging from 0 to 2,
with z+x═3.

19. The process according to claim 15, wherein the amine compound is an amine-based polymer, having a weight-average molecular weight ranging from 500 to 1 000 000.

20. The process according to claim 19, wherein the amine compound is an amine-based polymer selected from the group consisting of:
poly(($C_2$-$C_5$)alkyleneimines) and copolymers thereof;
polydimethylsiloxanes comprising primary amine groups at the chain end or on side chains of formula (A) or (B) or (C):

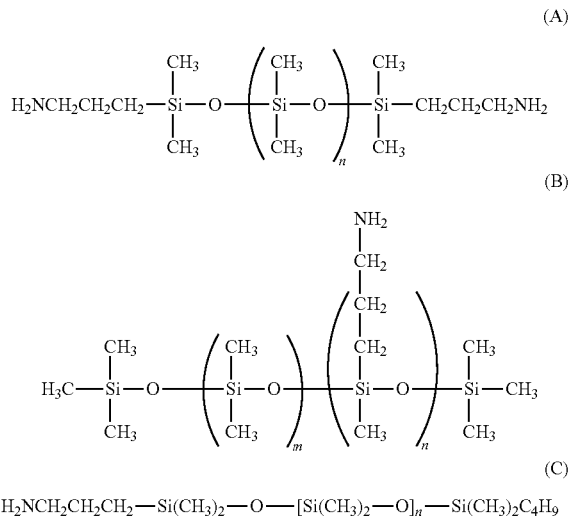

wherein:
in formula (A): the value of n is such that the weight-average molecular weight of the silicone is between 500 and 55 000;
in formula (B), the values of n and m are such that the weight-average molecular weight of the silicone is between 1000 and 55 000;
in formula (C), the value of n is such that the weight-average molecular weight of the silicone is between 500 and 3000;
amodimethicones of formula (D):

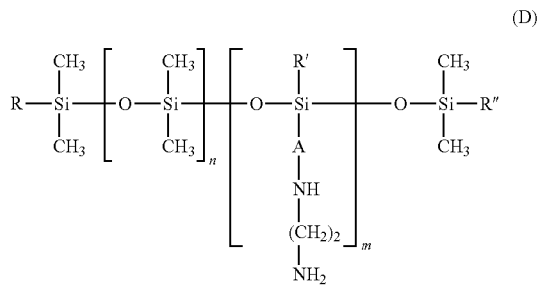

in which R, R' and R", which may be identical or different, each represent a $C_1$-$C_4$ alkyl or hydroxyl group, A represents a $C_3$ alkylene group and m and n are such that the weight-average molecular weight of the compound is between approximately 5000 and 500 000,
polyether diamines; polytetrahydrofuran α,ω-diamines, polytetramethylene glycol α,ω-diamines, or polybutadiene α,ω-diamines;
polyamidoamine dendrimers bearing amine end functions; and
poly(meth)acrylates or poly(meth)acrylamides bearing primary or secondary amine side functions.

21. The process according to claim 18, wherein the crosslinking agent is an amine compound selected from the group consisting of polydimethylsiloxanes comprising primary amine groups at the chain end or on side chains and 3-aminopropyltriethoxysilane.

22. The process according to claim 15, wherein the amine compound is used in a mole ratio of amine group of the amine compound/phosphonic acid of the polymer ranging from 0.01 to 10.

23. The process according to claim 18, wherein when the composition contains an amino alkoxysilane, it comprises a $C_2$-$C_5$ monoalcohol in a content ranging from 0.1% to 5% by weight relative to the total weight of the composition.

24. The process according to claim 15, wherein the additional compound is a plasticizer and the plasticizer is selected from the group consisting of tri-n-butyl citrate, tripropylene glycol monomethyl ether (INCI name: PPG-3 methyl ether) and trimethyl pentaphenyl trisiloxane and non volatile oil.

25. The process according to claim 1 wherein a clay selected from clays of the smectite family, of the kaolinite family, optionally modified clays of the halloysite, dombassite, antigorite, benthierine, pyrophyllite, montmorillonite, beidellite, vermiculite, talc, stevensite, hectorite, bentonite, saponite, chlorite, sepiolite and illite family is further applied to the hair.

26. The process according to claim 1 wherein a salt of divalent or trivalent metal ions selected from salts of ions derived from Al(III), Ca(II), Cu(II), Fe(II), Fe(III), Mg(II), Mn(II), Zn(II) and mixtures thereof is further applied to the hair.

27. The process according to claim 1 wherein a metal oxide selected from titanium dioxide, iron oxides, zirconium oxides, zinc oxides, cerium oxides and chromium oxides is further applied to the hair.

28. The process according to claim 18, wherein the composition is formed by mixing two different compositions between 1 minute and 24 hours before application to keratin materials.

29. The process according to claim 18, wherein the composition further comprises an oil.

30. A composition comprising (i) at least one pigment, (ii) at least one block polymer comprising:
at least one first block with a glass transition temperature (Tg) of greater than or equal to 40° C. and obtained from at least one (meth)acrylate monomer of formula $CH_2=C(R_1)-COOR_2$ in which $R_1$ represents H or a methyl radical and $R_2$ represents a $C_4$ to $C_{12}$ cycloalkyl group; and
at least one second block with a glass transition temperature (Tg) of less than or equal to 20° C. and is obtained from at least one vinylphosphonic acid monomer of formula (I) and from at least one (meth)acrylate monomer of formula $CH_2=C(R_1)-COOR_3$ in which $R_1$ represents H or a methyl radical and $R_3$ represents either a linear or branched $C_1$ to $C_6$ unsubstituted alkyl group, with the exception of a tert-butyl group or a methoxyethyl group;
said vinylphosphonic acid monomer of formula (I) being:

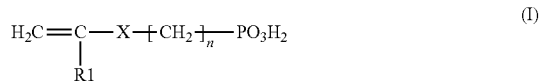

in which:

R1 denotes H or —CH$_3$;

X denotes a covalent bond and n denotes an integer ranging from 0 to 14;

or X denotes a —COO— group and n denotes an integer ranging from 2 to 6, and (iii) at least one additional compound selected from plasticizers and/or crosslinking agents.

31. The composition according to claim 30, wherein the block polymer is present in a content ranging from 0.1% to 40% by weight and the pigment is present in a content ranging from 0.5% and 40% by weight, all weights relative to the total weight of the composition.

\* \* \* \* \*